(12) United States Patent
Nagahara et al.

(10) Patent No.: US 7,504,553 B2
(45) Date of Patent: Mar. 17, 2009

(54) ABSORBENT ARTICLE

(75) Inventors: Shinsuke Nagahara, Tochigi (JP); Nobuya Sato, Tochigi (JP); Yayoi Fukuhara, Tochigi (JP); Ken Nemoto, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/206,044

(22) Filed: Aug. 18, 2005

(65) Prior Publication Data
US 2006/0041239 A1 Feb. 23, 2006

(30) Foreign Application Priority Data
Aug. 19, 2004 (JP) ............... 2004-239931

(51) Int. Cl.
*A61F 13/15* (2006.01)
*A61F 13/20* (2006.01)
(52) U.S. Cl. .................. 604/380; 604/378; 604/367
(58) Field of Classification Search ......... 604/378–380, 604/385.01, 385.101
See application file for complete search history.

(56) References Cited

U.S. PATENT DOCUMENTS

| | | | | |
|---|---|---|---|---|
| 3,736,931 A | * | 6/1973 | Glassman | 604/385.19 |
| 3,886,941 A | * | 6/1975 | Duane et al. | 604/370 |
| 4,781,710 A | | 11/1988 | Megison et al. | |
| 5,128,193 A | * | 7/1992 | Anapol et al. | 428/171 |
| 5,891,118 A | * | 4/1999 | Toyoshima et al. | 604/366 |

FOREIGN PATENT DOCUMENTS

| | | |
|---|---|---|
| JP | 61-85942 A | 5/1986 |
| JP | 6-315501 A | 11/1994 |
| JP | 2003-33397 A | 2/2003 |
| JP | 2003-38552 A | 2/2003 |
| WO | WO-97/24092 A1 | 7/1997 |
| WO | WO-02/085272 A1 | 10/2002 |
| WO | WO-03/017900 A1 | 3/2003 |

\* cited by examiner

*Primary Examiner*—Michele Kidwell
(74) *Attorney, Agent, or Firm*—Birch, Stewart, Kolasch & Birch, LLP

(57) ABSTRACT

An absorbent article having a topsheet 2, a backsheet 3, and an absorbent member 4 interposed between the topsheet 2 and the backsheet 3 is disclosed. The absorbent member 4 has a number of compressed parts 7 which are discrete from one another and concave on the backsheet facing side and/or the topsheet facing side. The compressed part is configured to increase in thickness on absorbing liquid. The compressed part is made up of a thinnest portion 8 and a sloping portion 9. The sloping portion a gradually changes in thickness to connect to the thinnest portion 8.

4 Claims, 4 Drawing Sheets

ABSORBENT ARTICLE

FIELD OF THE INVENTION

The present invention relates to absorbent articles including sanitary napkins, panty liners, vaginal discharge sheets, incontinence pads and disposable diapers.

BACKGROUND ART

Absorbent articles the absorbent member of which has an embossed pattern of a number of discrete depressed areas are known. For example, JP-A-2003-33397 proposes an absorbent article having its thickness reduced by embossing the absorbent member thereof while retaining the softness of the absorbent member in terms of elasticity and deformability. In a plan view, the individual embossed depressions contain no straight line nor a concave curve in their outline. The proposed absorbent article is described as having its thickness reduced easily while retaining softness.

U.S. Pat. No. 4,781,710 discloses an absorbent pad having a densification pattern comprising relatively low density tuft regions which are separated and surrounded by channels. The channel comprises storage regions and transport regions wherein one of the storage regions and the transport regions separate and surround the other of the storage regions and the transport regions. The transport regions have a density greater than the density of the storage regions which, in turn, have a density greater than the tuft regions. The absorbent pad is described as having improved liquid distribution and retention characteristics.

WO97/24092 proposes an absorbent article comprising a topsheet and an absorbent core, the core having at least two depressed areas forming channels, and the topsheet being permanently joined to the core in the depressed areas. The absorbent article is described as having an acceptable fluid transfer profile from the topsheet to the core.

According to JP-A-2003-33397, the thickness of the absorbent member is reduced by forming an embossed pattern with no concavity in its plan. Strong embossing pressure should be imposed to the bottom of the depressions to form a pattern with no concavity. As a result, the depressed regions exhibit little absorptivity. Moreover, the aim of the invention is to provide a soft absorbent member with no consideration given to liquid distribution in the absorbent member.

According to U.S. Pat. No. 4,781,710, transport regions and storage regions are provided in the continuous channels in such a configuration that one of the storage regions and the transport regions separate and surround the other. This configuration allows for easy transfer of liquid to the storage regions having small absorbent capacity within the channels. However, the large and drastic density difference between the channels and the tuft regions having high absorbent capacity hampers smooth liquid transfer so that the absorbent pad fails to secure sufficient absorbent capacity at and in the vicinity of a liquid absorption point.

The structure of WO97/24092 has the same problem as U.S. Pat. No. 4,781,710 on account of the depressed areas forming continuous channels. That is, it is difficult to cause liquid to move from the channels to the surrounding absorbent member taking advantage of the density difference. In addition, liquid retention in the channels is not assured because a part of a channel having absorbed liquid adjoins a part of the channel not having absorbed liquid.

SUMMARY OF THE INVENTION

The present invention provides an absorbent article having a topsheet, a backsheet, and an absorbent member interposed between the topsheet and the backsheet. The absorbent member has a backsheet facing side and a topsheet facing side. The absorbent member also has a number of compressed parts which are discrete from one another and concave on the backsheet facing side and/or the topsheet facing side thereof. The compressed parts are configured to increase in thickness on absorbing liquid.

DETAILED DESCRIPTION OF THE INVENTION

The present invention will be described based on its preferred embodiments with reference to the accompanying drawings.

FIRST EMBODIMENT

Figure 1:
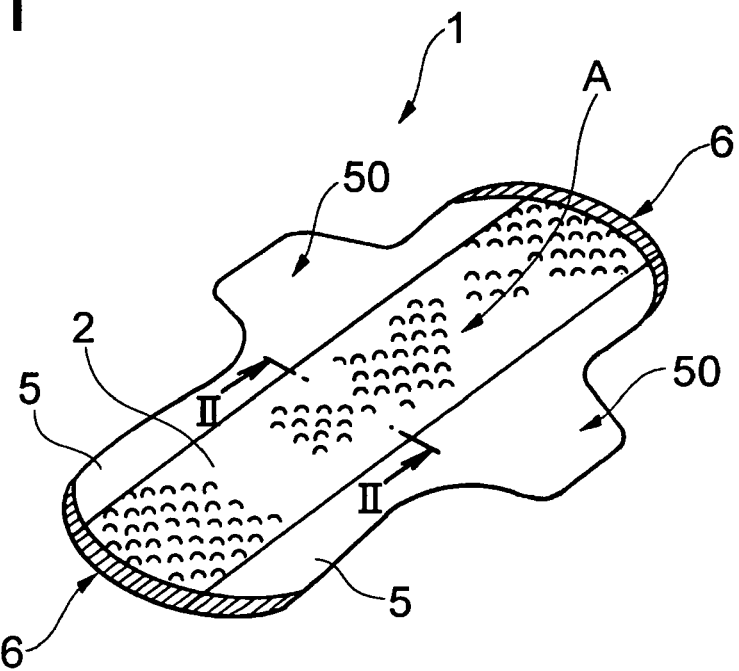
FIG. 1 is a perspective view of a sanitary napkin as a first embodiment of the present invention.
Figure 2:
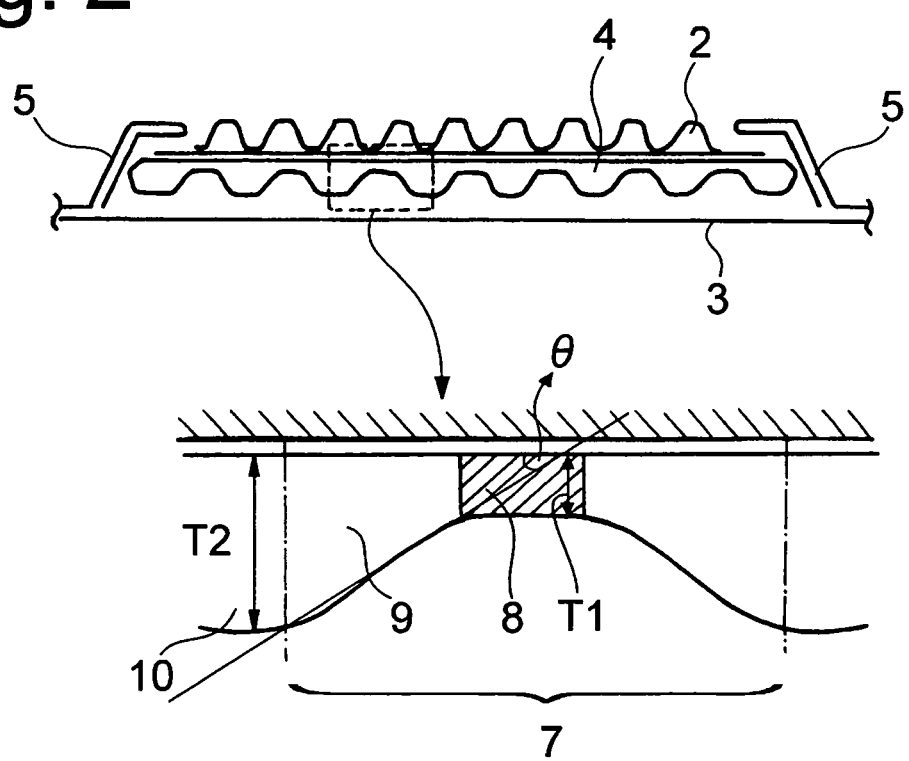
FIG. 2 is a cross-sectional view of FIG. 1 along line II-II and its partial enlarged view.

FIGS. 1 and 2 illustrate a sanitary napkin 1 according to the first embodiment of the invention. As shown, the sanitary napkin 1 is substantially longer than is wide and has a topsheet 2, a backsheet 3, and an absorbent member 4 interposed between the two sheets. The napkin 1 additionally has a pair of side sheets 5 on both longer sides thereof on the skin facing side thereof. The side sheets 5 and the backsheet 3 extend outward from the long side edges of the absorbent member 4 and joined together at their extensions to form a pair of wings 50. The topsheet 2 and the backsheet 3 extend outward from the short side edges of the absorbent member 4 and joined together at their extensions to form end seals 6.

The topsheet 2 is permeable to liquid. Perforated or non-perforated nonwoven fabric or perforated film is a preferred topsheet 2. The nonwoven fabric can be of single or conjugate fibers of synthetic resins, such as polyolefins, e.g., polyethylene and polypropylene, polyester, polyamide, and polyurethane. Natural or regenerated fibers such as cotton and rayon are also useful. These fibers are carded or air-laid to form a web, which is made into nonwoven fabric by through-air processing, heat roll processing (heat embossing) or hydro-entangling processing, or the fibers are converted to a web by spun-laying or melt-blowing, which is then made into nonwoven fabric.

As illustrated in FIG. 2, the topsheet 2 has a number of projections on its skin facing side. The topsheet 2 is prepared by embossing a bulky nonwoven fabric, for example, an air-through nonwoven fabric of sheath-core conjugate fiber composed of a polyethylene sheath and a polyethylene terephthalate core, from the skin facing side. The topsheet 2 is thus superior in dry and cushioning feel. Flat on the absorbent member-facing side, the topsheet 2 is in close contact with the absorbent member 4 to assure good liquid transfer to the absorbent member 4.

The backsheet 3, which is impermeable to liquid, can be formed of, for example, a polyolefin resin (e.g., polyethylene or polypropylene) sheet or a hydrophobic or water-repellent nonwoven fabric either alone or in combination. A moisture permeable sheet obtained by stretching an olefin resin film loaded with an inorganic filler or a spunbonded-meltblown-spunbonded (SMS) nonwoven fabric is a preferred backsheet 3 which can reduce skin overhydration. In using a nonwoven fabric as a backsheet 3, it is preferred to partly enhance the leakproof function by covering the central region of the napkin 1 with a resin sheet or applying a hot melt adhesive to the central region. The backsheet 3 used in the present embodiment is a moisture permeable sheet obtained by stretching a polyethylene film loaded with an inorganic filler. Where a liquid impermeable sheet is laid on the absorbent member side of the backsheet 3, the backsheet 3 does not need to have liquid impermeability.

The absorbent member 4 comprises a fluff pulp aggregate and a superabsorbent polymer dispersed therein, entirely enveloped in thin absorbent paper. The superabsorbent polymer may be mixed up with pulp or sprinkled over the backsheet or inserted in a layer form in the middle of the thickness of the pulp aggregate. The superabsorbent polymer may be disposed in a desired area in the form of, e.g., a polymer sheet prepared in a known manner. While the fluff pulp aggregate may be used as such, it is preferred for the absorbent member 4 to be partly or entirely wrapped in a thin sheet, such as absorbent paper or nonwoven fabric, to prevent fall-off of the superabsorbent polymer particles. If desired, the wrapping sheet may be perforated or hydrophilized to improve liquid perviousness. Synthetic fiber or bulky pulp fiber having been crosslinked may be incorporated into the absorbent member 4 to help the compressed parts restore on liquid absorption. The superabsorbent polymer is not an essential component.

As shown in FIG. 2, in the absorbent member 4 of the present embodiment, a number of compressed parts 7 that are concave from the backsheet side through the wrapping absorbent paper (not shown) are discrete from one another and scattered all over the absorbent member 4. As illustrated in the enlarged view of FIG. 2, each compressed part 7 is made up of a thinnest portion 8 and a sloping portion 9. The part other than the compressed parts 7 is a non-compressed part 10 which is thickest between adjacent compressed parts. The sloping portion 9 has a gradual slope and gradually changes in thickness to connect to the thinnest portion 8. The sloping portion 9 smoothly connects the thinnest portion 8 having a thickness T1 and the non-compressed part 10 having a thickness T2. To secure high restoration on liquid absorption without destroying the structure of the thinnest portion 8, the angle θ between the topsheet side surface plane of the absorbent member and a line, which is defined by connecting the side end of the thinnest portion 8 and the side end of the sloping portion 9, is preferably 5° to 60°, more preferably 7° to 45°, even more preferably 10° to 30°. The compressed parts 7 are concave only on the backsheet side so that the topsheet side of the absorbent member remains almost flat.

Since the compressed parts 7 are discrete from each other, the structure from the non-compressed part 10 to the thinnest portion 8 is continuous along the entire periphery of the individual compressed parts 7. The compressed part 7 is configured to increase in thickness on liquid absorption. This phenomenon is also referred to as "restoration". Owing to that configuration, the compressed part 7 exhibits an enhanced liquid retentive function after liquid absorption to reduce wet-back and a wet feel of the topsheet 2. As the thickness of the compressed part 7 approaches that of the non-compressed part 10, the liquid moves to the non-compressed part 10 more easily. Thus, the region of the absorbent member 4 near the point of liquid absorption is made effective use of, and the liquid retentive function is further improved.

Additionally, the following four structural features of the absorbent member 4 produce the respective effects. Firstly, since the compressed part 7 has the sloping portion 9 with a gentle curve, there is no discontinuance in the absorbent structure, and restoration occurs easily. As a result, the absorbent member 4 exhibits an improved liquid retentive function. Secondly, the sloping portion 9 with a gradually changing thickness provides a density gradient between the non-compressed part 10 and the thinnest portion 8. Liquid drawn from the topsheet 2 to the absorbent member 4 is thus swiftly led to the thinnest portion 8. As a result, liquid is easily drawn from the topsheet 2 to reduce the wet feel of the topsheet 2. Thirdly, since the absorbent member 4 is flat on its topsheet side, it is in good contact with the topsheet 2, allowing the fluid having passed through the topsheet 2 to be quickly led to the absorbent member 4. As a result, fluid hardly spreads in the topsheet 2, which further reduces the wet feel of the topsheet 2. Fourthly, because a superabsorbent polymer is distributed in the absorbent member 4, the superabsorbent polymer disposed in the compressed part 7 is allowed to absorb liquid smoothly upon restoration of the compressed part 7, resulting in a further enhanced liquid retentive effect.

Figure 3:
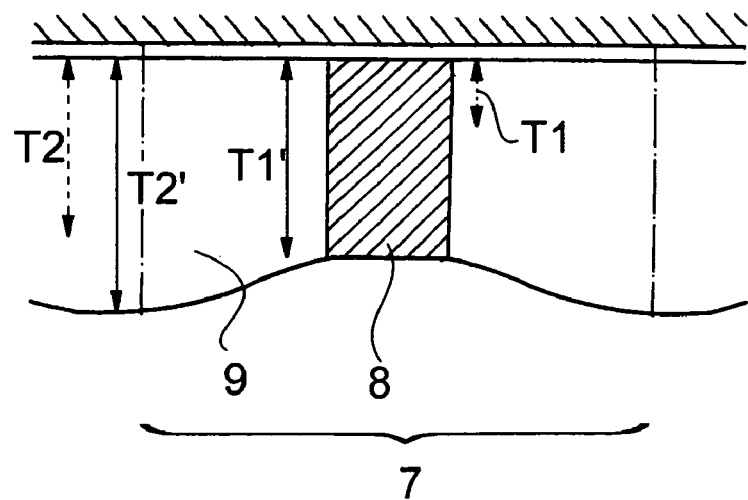
FIG. 3 is a partial enlarged cross-sectional view of FIG. 1 along line II-II illustrating the state of the absorbent member after liquid absorption.

The thickness T1 of the thinnest portion 8 before liquid absorption is preferably in a range of from 10% to 60%, more preferably 10% to 50%, even more preferably 15% to 40%, of the maximum thickness T2 of the non-compressed part 10 before liquid absorption so as to increase the liquid drawing properties and to secure thickness restoring capabilities of the compressed parts 7. As imaged in FIG. 3, it is preferred that the thickness T1 of the thinnest portion 8 before liquid absorption increase 1.5 to 15 times, more preferably 2 to 10 times, to a thickness T1' on liquid absorption.

The relationship between the maximum thickness T2 of the non-compressed part 10 before liquid absorption and the maximum thickness T2' after liquid absorption varies depending on whether a superabsorbent polymer is disposed in the absorbent member 4. Where a superabsorbent polymer exists, T2' is equal to or larger than T2 and preferably 1 to 10 times T2. Where a superabsorbent polymer does not exist, T2' is 0.7 to 1 times T2 due to collapse of the absorbent member (particularly pulp fibers) except where the absorbent member is fabricated using fiber having high compressive elasticity and has been wholly compressed so as to restore its thickness on getting wet (in which case the T2/T2' relationship is the same as in the case of using a superabsorbent polymer). Comparing T1' (the thickness of the thinnest portion 8 after liquid absorption) with T2' (the maximum thickness of the non-compressed part 10 after restoration on liquid absorption), because the absorbent structure has continuity from the thinnest portion 8 in the compressed part 7 to the non-compressed part 10 via the sloping portion 9, that is, because there is no abrupt change in density in the absorbent structure, the restoring capability of the absorbent member 4 is equal irrespective of whether a superabsorbent polymer is disposed or not. T1' is preferably 50% to 90%, more preferably 60% to 85%, even more preferably 65% to 80%, of T2' irrespective of whether the non-compressed part 10 increases or decreases, or does not change, in thickness on liquid absorption. Where a superabsorbent polymer is disposed in the absorbent member 4, naturally the absorbent member 4 exhibits markedly increased absorption capacity.

In this particular embodiment T2' (maximum thickness of the non-compressed part 10 after liquid absorption) is greater than T2 (maximum thickness of the non-compressed part 10 before liquid absorption) primarily because of the swell of the superabsorbent polymer. For example, an absorbent member comprising a pulp having a basis weight of 100 to 400 g/m$^2$ and a superabsorbent polymer having a basis weight of 20 to 50 g/m$^2$ increases in thickness to about 1.2 to 3.0 times T2 on liquid absorption. With a higher superabsorbent polymer content, the thickness further increases.

The thickness T1 of the compressed part 7 before liquid absorption is preferably 0.3 to 3 mm. The thickness T2 of the non-compressed part 10 before liquid absorption is preferably 1 to 10 mm for maintaining softness of the absorbent member 4. The basis weight of a pulp in the absorbent member 4 is preferably 100 to 400 g/m$^2$, more preferably 150 to 300 g/m$^2$. The absorbent member 4 before liquid absorption preferably has a density of 0.1 to 0.6 g/cm$^3$ in its compressed parts 7 and of 0.01 to 0.1 g/cm$^3$ in its non-compressed part 10.

Methods of forming the compressed parts 7 include a heat embossing method in which an absorbent member is passed through the nip between an embossing roll having projections discrete from one another and heated to 100° C. or higher and a flat backup roll with a given nip gap to form the thinnest portions 8 and a compressive embossing method wherein an embossing roll having projections each having a highest top and a sloping region and heated to a temperature lower than 100° C. is used to form the thinnest portions 8 and the sloping portions 9. Also useful is a water-soluble adhesive method wherein a hydrophilic adhesive component (e.g., a hydrophilic adhesive, hydrophilic synthetic fibers or hydrophilic resin particles) is incorporated into the absorbent member or partially applied to the absorbent member so as to immobilize the thinnest portions when compressed. These methods can be used either individually or as an arbitrary combination thereof.

The absorbent member 4 used in the first embodiment is obtained by the heat embossing method in which the heated embossing roll is placed on the backsheet side. In order to form the gently sloping portions 9 with ease, the heat embossing is carried out in such a fashion that the region other than the standing pins of the embossing roll is in contact with the absorbent member and the whole adsorbent member (especially the non-compressed part) is temporarily compressed (partial compression). For the same purpose, it is also possible that the absorbent member is lightly compressed by, for example, passing through a pair of rolls prior to the partial compression to adjust the thickness of the absorbent member so that the region other than the compressed parts may not be compressed in the partial compression step and, after the partial compression, the portion other than the thinnest portions is allowed to restore its bulk to form the gently sloping portions 9. The method in which the whole absorbent member is compressed by the overall compression followed by partial compression with an embossing roll, etc. is the most preferred method for forming gently sloping portions 9. Incorporating a hydrophilic adhesive component into the absorbent member 4 is the most preferred method for stably fixing the thinnest portions 8 until liquid absorption. In order to facilitate forming a flat surface on the topsheet side of the absorbent member 4, it is possible to use a backup roll having recesses corresponding to the pins on the embossing roll. In the present invention, the region between adjacent compressed parts where the thickness is the largest is named "a non-compressed part" even though it has been somewhat compressed.

The center-to-center distance between adjacent compressed parts is preferably 1 to 10 mm, more preferably 2 to 7 mm, even more preferably 3 to 6 mm, to secure liquid drawing properties without making the absorbent member 4 too hard. In order for the compressed parts 7 to stably retain their shape until liquid absorption and to restore easily on liquid absorption, the thinnest portion 8 preferably has a length of 0.5 to 4 mm, more preferably 1 to 3 mm, measured on an extension of the shortest line connecting adjacent compressed parts.

T2, the maximum thickness of the non-compressed part 10, is preferably at the middle of the shortest line connecting adjacent compressed parts 7. For retaining the softness of the absorbent member 4, T2 is preferably present over a length of 50% or shorter, more preferably 20% to 40%, of the above-mentioned shortest line. For improving liquid distribution and the properties of drawing liquid from the topsheet 2, on the other hand, T2 is preferably present over a length of 0 up to 20%, more preferably 0 to 5%, of the shortest line. The non-compressed part 10 adjoins the sloping portions 9 on the shortest line connecting the compressed parts. The non-compressed part 10 has an almost uniform thickness (T2) on the shortest line but may have a varying thickness along other lines.

The shape of the individual compressed parts 7 in the plan view includes circles, ellipses, triangles, and rectangles. The central part of the thinnest portion 8 may be hollowed to facilitate restoration of the compressed part 7. The pattern of discretely arranging the compressed parts 7 includes a rhombic lattice pattern and a square lattice pattern. Because liquid spreads from one compressed part to another, it is desirable for preventing side leakage that the compressed parts 7 be arranged such that a line connecting compressed parts 7 that are nearest to each other may not be straight in the width direction of the absorbent member. In other words, the compressed parts 7 are preferably arranged at random (for example, a line connecting the nearest compressed parts 7 is oblique to the width direction), or arranged in such a manner that a line connecting the nearest compressed parts 7 makes an angle of 30° to 60° to the width direction.

As previously stated, the topsheet 2 used in the first embodiment has projections on its skin facing side. For helping discharged fluid quickly move downward without staying in the topsheet 2, it is preferred to use, as the topsheet 2, a double-layered sheet or a combination of two layers partly joined together to create a capillarity gradient due to a gradient in density or hydrophilicity allowing for easy liquid transfer from the upper to the lower layers.

The side sheet 5 can be selected according to desired functions from among water-repellent nonwoven fabrics, hydrophilic nonwoven fabrics, nonwoven fabric/film laminates, perforated or non-perforated films, and the like. Water-repellent nonwoven fabrics are preferred for their pleasant feel and blocking properties against penetration of fluids, such as menstrual blood and other discharges. Hydrophilic nonwoven fabrics are used when the lateral sides of the napkin 1 are expected to have absorptivity. Where both absorptivity and leakproofness are desired, a nonwoven fabric/film laminate is preferably used with the nonwoven fabric facing the skin. Where liquid permeability is desired, a perforated film is preferably used. In using a nonwoven fabric/film laminate, the feel to the touch can be improved by joining the nonwoven fabric and the film by spot bonding. In the first embodiment, the side of the SMS nonwoven fabric nearer to the widthwise middle of the napkin 1 is folded back to make a double ply structure as illustrated in FIG. 2. The folded portion of the fabric may be joined to itself in a pattern such as a floral pattern to give an aesthetic look. The topsheet 2 and the double-ply structure of the side sheet 5 are joined together at their overlap with a hot-melt adhesive continuously applied in the longitudinal direction.

SECOND EMBODIMENT

Figure 4A:
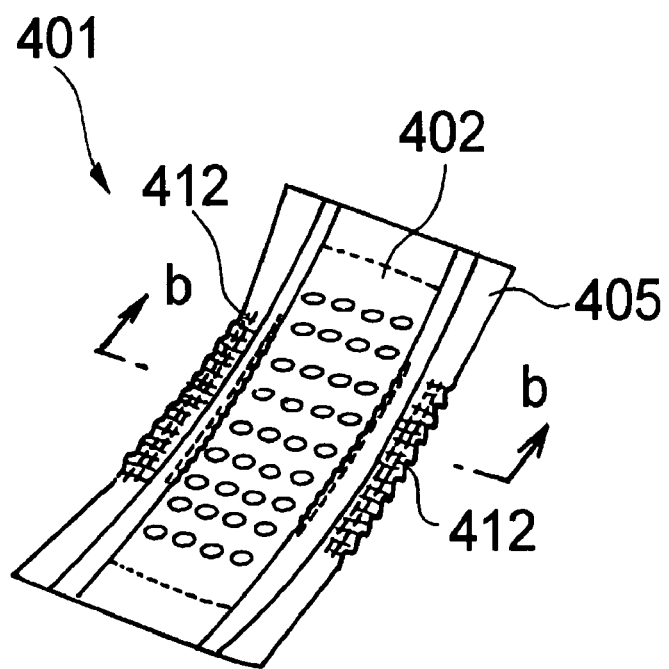
FIG. 4(a) is a perspective view of a disposable diaper as a second embodiment of the present invention.
Figure 4B:
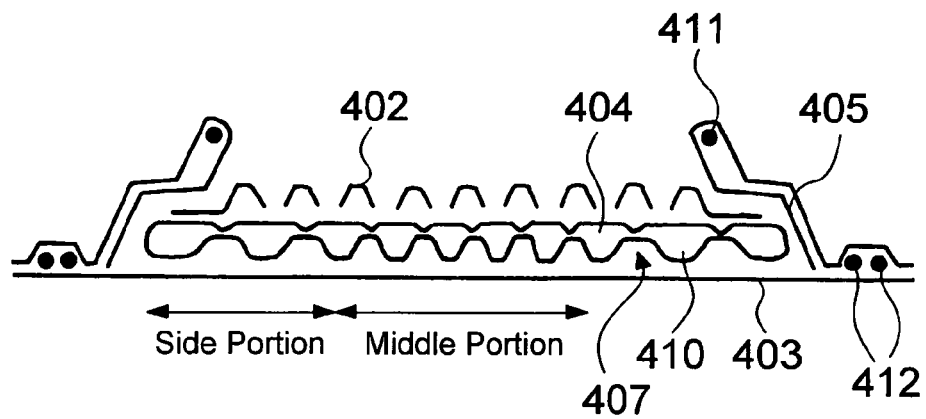
FIG. 4(b) is a cross-sectional view of FIG. 4(a) taken along line b-b.
Figure 4C:
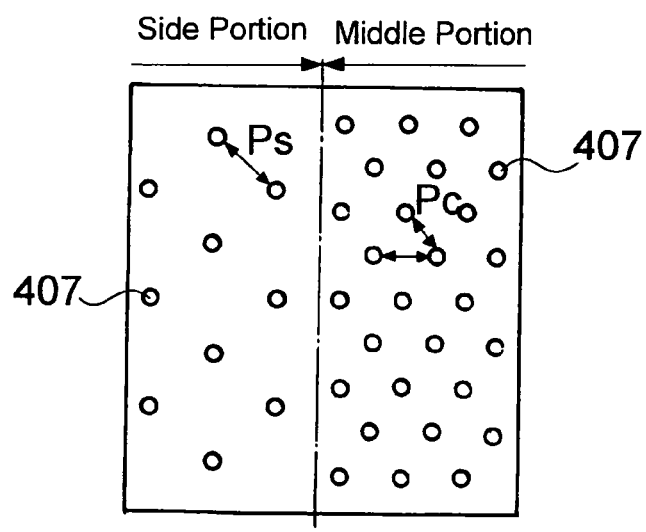
FIG. 4(c) illustrates the pattern of compressed parts arranged in the absorbent member of FIG. 4(b).

FIGS. 4(a), 4(b), and 4(c) represent a disposable diaper 401 as a second embodiment of the absorbent article according to the present invention. The disposable diaper 401 has a topsheet 402, a backsheet 403, and an absorbent member 404. The topsheet 402 is a perforated nonwoven fabric. The perforated nonwoven fabric is obtained by, for example, converting polyethylene sheath-polypropylene core conjugate fiber into bulky nonwoven fabric by through-air processing and passing the nonwoven fabric between a perforating pin roll heated close to the melting point of polyethylene and a backup roll. The area where a pin has pierced through forms a rib of a perforation. The perforating pin roll is applied to the skin facing side of the nonwoven fabric. The backsheet 403 is an SMS nonwoven fabric/moisture permeable film laminate which is obtained by stretching a polyethylene film loaded with an inorganic filler to prepare a moisture permeable film, spraying a hot-melt adhesive to the film, and joining a polypropylene SMS nonwoven fabric to the film via the adhesive.

An SMS nonwoven fabric folded in two is provided as a side sheet 405 on both lateral sides of the topsheet side of the diaper 401. An elastic member 411 is disposed within the fold so that the free end of the fold (the side sheet 405) may gather to form a standing cuff. The side sheet 405 is bonded to the topsheet 402 at the foot of the standing cuff. The side sheet 405 and the backsheet 403 each have an extension extending from the side edge of the absorbent member 4 and bonded to each other at their extensions to form a leg flap. Elastic members 412 are disposed in the leg flap to form leg gathers helping provide a snug fit to the body contour.

The absorbent member 404 used in the second embodiment is an aggregate of fluff pulp having a superabsorbent polymer dispersed therein. The absorbent member 404 is sectioned into a widthwise middle portion and a side portion located by both long sides of the middle portion. As illustrated in FIG. 4(c), the distance between adjacent compressed parts 407 is different between the middle portion and the side portions. The thicknesses of the compressed part 407 and the non-compressed part 410 are equal between the middle portion and the side portion. Therefore, both the middle portion and the side portion exhibit restoration at the compressed parts 407 on liquid absorption to develop liquid absorbing performance. Even if the non-compressed part 410 in the middle portion and that in the side portion are different in thickness because of the difference in the distance of adjacent compressed parts 407, every compressed part 407 exhibits thickness restoration to develop liquid absorbing performance.

The distance Pc between adjacent compressed parts in the middle portion is smaller than the distance Ps between adjacent compressed parts in the side portion. As a result, liquid diffuses more easily in the middle portion than in the side portions so that the middle portion has higher capability of drawing liquid from the topsheet than the side portions. Furthermore, liquid is allowed to diffuse easily in the length direction of the absorbent member, resulting in increased utility of the absorbent member. On the other hand, liquid distribution is suppressed in the side portions compared with the middle portion, securing protection against side leakage. The distance Pc is preferably 1 to 8 mm, more preferably 2 to 5 mm. With the distance Pc being in that range, the length of the non-compressed part 410 between adjacent compressed parts in the middle portion is made close to zero, resulting in further secured liquid distribution. The distance Ps in the side portions is preferably 1 to 10 mm, more preferably 2 to 7 mm.

The absorbent member 404 used in the second embodiment has compressed parts 7 which are not only concave on the backsheet side similarly to the first embodiment but also shallowly concave on the topsheet side. In using an absorbent member with such an uneven surface on the topsheet side, the contact with the topsheet can be improved by, for example, (1) interposing a cushioning intermediate sheet between the absorbent member 404 and the topsheet 402, (2) applying an adhesive in a spiral pattern to partly join the topsheet 402 to the absorbent member 404 or (3) embossing the absorbent member 404 and the topsheet 402 from the side of the topsheet to form grooves, etc.

THIRD EMBODIMENT

A third embodiment of the present invention provides a sanitary napkin having the same basic structure as the first embodiment, being composed of a topsheet, a backsheet, a pair of side sheets, and an absorbent member. The topsheet is, for example, a perforated polyethylene film. The backsheet is, for example, a polyethylene film embossed in a dot pattern. The side sheet is, for example, an SMS nonwoven fabric with one of the long side portions thereof folded back.

Figure 5:
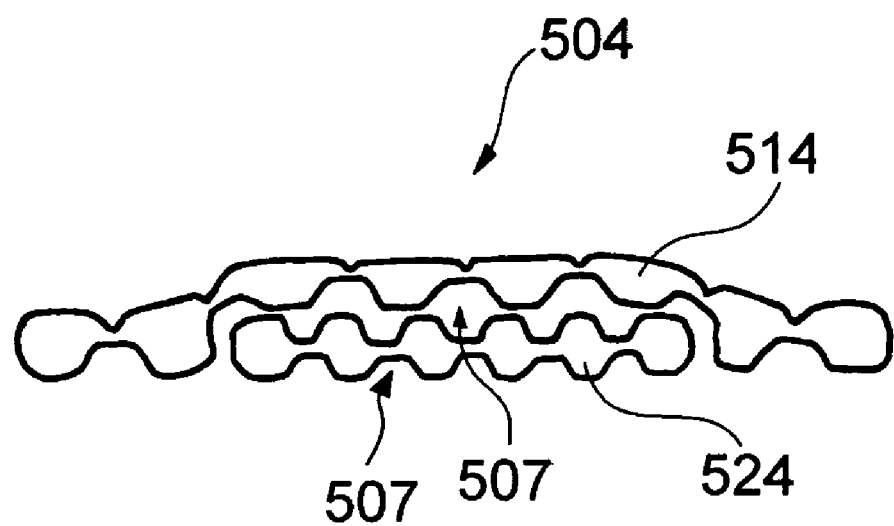
FIG. 5 is a cross-sectional view of an absorbent member used in a sanitary napkin as a third embodiment of the present invention.

FIG. 5 shows the absorbent member 504 used in the third embodiment. The absorbent member 504 is composed of an upper layer 514 and a lower layer 524. The upper layer 514 exists over the entire area of the absorbent member 504, while the lower layer 524 is disposed under the upper layer 514 (i.e., farther from the topsheet than the upper layer 514) only in the region corresponding to the target zone where a body fluid discharge will be located. The upper layer 514 and the lower layer 524 are each heat-embossed to have elliptic compressed parts 507 of a size, but the lower layer 524 has more compressed parts 507 per unit area than the upper layer 514. This means that the lower layer 524 exhibits higher capability of drawing liquid than the upper layer 514 and that liquid is easily transferred from the upper layer 514 to the lower layer 524, not allowing liquid to remain in the topsheet. Moreover, the upper layer 514 has fewer compressed parts 507 than the lower layer 524, which is effective to suppress liquid spread in the upper layer 514.

The upper layer 514 and the lower layer 524 are both made of pulp and a superabsorbent polymer. While other materials than the pulp and the superabsorbent polymer are not used, the two layers may be separately wrapped in respective absorbent paper sheets and then superposed on each other, or the two layers are superposed and then wrapped together in absorbent paper. Synthetic fiber may be incorporated in a proportion of 30% by weight or less to improve thickness restoring properties of the compressed parts on liquid absorption.

In the third embodiment, the topsheet and the upper layer 514 of the absorbent member 504 are joined together by embossing to form a groove having the shape of an elongated circle in its plan view on the topsheet side of the napkin. In the area surrounded by the groove, the topsheet and the upper layer 514 are also joined in a dot pattern by the embossing. The groove is preferably along a line adjoining the periphery of the overlap of the upper layer 514 and the lower layer 524. By so locating the groove, the topsheet and the upper layer 514 can be brought into good contact to improve the properties of drawing liquid from the topsheet. The location of the groove is also effective to prevent the upper layer 514 and the lower layer 524 from getting out of alignment while the sanitary napkin is worn or during making the absorbent member 504.

The upper layer 514 has a number of compressed parts that are concave on both the topsheet and the backsheet sides thereof. The depth of the concavity on the topsheet side is smaller than that on the backsheet side. The ratio of the depth on the topsheet side to the depth on the backsheet side is about 1:3 to 1:5. The lower layer 524 also has a number of compressed parts that are concave on both the topsheet and the backsheet sides thereof. The depth of the concavity on the topsheet side and that on the backsheet side are nearly equal. The ratio of the depth on the topsheet side to the depth on the backsheet side is about 3:5 to 5:3. The compressed parts of the upper and the lower layers being so configured as described above, the stability of the contact between the upper layer 514 and the lower layer 524 is improved to prevent the two layers from getting out of alignment, and liquid transfer from the upper layer 514 to the lower layer 524 is improved.

FOURTH EMBODIMENT

The present invention provides in its fourth embodiment a sanitary napkin having the same structure as the first embodiment, except that a polymer sheet is superposed on the backsheet side of the absorbent member 4. The polymer sheet is a laminate of two sheets of absorbent paper having fixed therebetween a layer of a superabsorbent polymer via a spirally applied pressure-sensitive adhesive. The absorbent member 4 used in the fourth embodiment contains no superabsorbent polymer and, instead, contains an adhesive fiber such as polyvinyl alcohol fiber. The absorbent member is heat-embossed in the same manner as in the first embodiment prior to superposing the polymer sheet. The heat embossing results in formation of compressed parts by taking advantage of the adhesiveness of the polyvinyl alcohol fiber. Containing no superabsorbent polymer, the absorbent member reduces in thickness in the non-compressed part on absorbing liquid by about 10% to 20%. On the other hand, the thickness of the compressed part increases on liquid absorption to 2 to 10 times the thickness of the compressed part before liquid absorption. The thickness of the compressed part after liquid absorption reaches 50% to 90% of the thickness of the non-compressed part after liquid absorption. In the compressed parts, the polyvinyl alcohol fiber reduces in adhesiveness on liquid absorption thereby allowing the compressed parts to increase their thickness.

While the present invention has been described in detail with reference to its preferred embodiments, it should be understood that various changes and modifications can be made therein without departing from the spirit and scope thereof. For example, the distance between compressed parts adjacent in the length direction of an absorbent article can be reduced to help liquid be distributed in the length direction. When the compressed parts have an elliptic shape or a like elongated shape, the direction of liquid distribution can be controlled by arranging the compressed parts with their major axis directed lengthwise, widthwise or obliquely without varying the distance between adjacent compressed parts.

The non-compressed part of an absorbent member may have its thickness varied from place to place. For that purpose, the distance between adjacent compressed parts and/or the minimum thickness of the compressed parts can be varied from place to place.

The description of the first embodiment applies appropriately to those details of the second to the fourth embodiments which are not particularly mentioned here.

In the present invention the degree of thickness restoration in the compressed and the non-compressed parts on liquid absorption is evaluated in accordance with the method described below using simulated blood prepared as follows.

Measurement of Thickness Before and after Liquid Absorption

A microscope VH-8000 from Keyence Corp. was used at a magnification of 50 times to observe a cut area of a sample. A razor FAS-10 from Feather Safety Razor Co., Ltd. was used to cut the sample to provide a cut area.

A cut area of a sample absorbent member before liquid absorption, which cut area should represent the thicknesses of the compressed and the non-compressed parts of the sample, is photographed. Ten drops of simulated blood (totalizing 0.77 g) are dropped on the cut non-compressed part on the topsheet side within 10 seconds. Thirty seconds after the addition, the same site of the cut area as photographed before liquid absorption is photographed again. The thickness of the thinnest portion of the compressed parts and the thickness of the non-compressed part before and after liquid absorption are measured on the photographs.

Preparation of Simulated Blood

In a 2 liter beaker is put 1500 g of ion exchanged water, and 5.3 g of sodium carboxymethyl cellulose (CMC-Na, from Kanto Kagaku) is dissolved therein by stirring with a magnetic stirrer to prepare solution A. In a 1 liter beaker is put 556 g of ion exchanged water, and 27.0 g of sodium chloride (from Kanto Kagaku) and 12 g of sodium hydrogencarbonate (from Kanto Kagaku) are completely dissolved therein by stirring with a stirrer to prepare solution B.

Into a 3 liter beaker is charged 900 g of glycerin, and solutions A and B were added and stirred. To the mixture are added 15 ml of an aqueous solution of a nonionic surface active agent Emulgen 935 (from Kao Corp.) (surface active agent/water=1 g/l) and 0.3 g of FD & C Red No. 2 (available from Aizen Hodogaya Co., Ltd., manufactured by Daiwa Kasei K.K.), followed by stirring. The mixture is filtered by suction through a glass filter. The filtrate is used as simulated blood. Emulgen 935 may be replaced with other nonionic surface active agent to prepare simulated blood, but it should be noted that the amount must be adjusted so that the resulting simulated blood may form a contact angle with glass of 35° to 40°. The contact angle with a glass substrate is measured with a face contact angle meter (CA-A, from Kyowa Interfacial Science Co., Ltd.). The glass substrate is used after cleaning with ethanol.

As described, the absorbent member used in the absorbent article of the present invention exhibits excellent performance in drawing liquid from the topsheet and retaining liquid near the point of absorption. Thus, the absorbent article according to the present invention prevents wet-back and leakage and provides a comfort and a dry feel.

What is claimed is:

1. An absorbent article comprising a topsheet, a backsheet, and an absorbent member interposed between the topsheet and the backsheet, the absorbent member having a backsheet facing side and a topsheet facing side, the absorbent member having a number of compressed parts which are discrete from one another and form concavities that are scattered on the backsheet facing side of the absorbent member, and the compressed parts being configured to increase in thickness on absorbing liquid, wherein the number of compressed parts comprise a thinnest portion and a sloping portion, and the sloping portion gradually changes thickness to connect to the thinnest portion, wherein the absorbent structure has continuity from the thinnest portion in the compressed part to a non-compressed part via the sloping portion without abrupt change in density in the absorbent structure, wherein the angle θ between the topsheet side surface plane of the absorbent member and a line, which is defined by connecting the side end of the thinnest portion of each compressed part and the side end of the sloping portion of each compressed part, before absorbing liquid, is 5° to 60°, wherein the compressed parts are concave only on the backsheet facing side and the topsheet facing side of the absorbent member remains almost flat, and wherein the absorbent member is an aggregate of fluff pulp having a superabsorbent polymer dispersed therein.

2. The absorbent article according to claim 1, wherein the compressed part is configured to increase in thickness on liquid absorption such that the thickness of the compressed part increases 1.5 to 15 times.

3. The absorbent article according to claim 1, wherein the absorbent member further has a non-compressed part, the non-compressed part is configured to increase in thickness on liquid absorption, and the thickness of the compressed part after liquid absorption is 50% to 90% of the thickness of the non-compressed part after liquid absorption.

4. The absorbent article according to claim 1, wherein the absorbent member further has a non-compressed part, the non-compressed part is configured to reduce or not to change in thickness on liquid absorption, and the thickness of the compressed part after liquid absorption is 50% to 90% of the thickness of the non-compressed part after liquid absorption.

* * * * *